United States Patent
Desrochers

(10) Patent No.: US 9,651,531 B2
(45) Date of Patent: May 16, 2017

(54) AIR SAMPLING SYSTEM PROVIDING COMPOUND DISCRIMINATION VIA COMPARATIVE PID APPROACH

(71) Applicant: Aircuity, Inc., Newton, MA (US)

(72) Inventor: Eric M. Desrochers, Merrimack, NH (US)

(73) Assignee: Aircuity, Inc., Newton, MA (US)

( * ) Notice: Subject to any disclaimer, the term of this patent is extended or adjusted under 35 U.S.C. 154(b) by 846 days.

(21) Appl. No.: 13/930,017

(22) Filed: Jun. 28, 2013

(65) Prior Publication Data

US 2015/0004898 A1 Jan. 1, 2015

(51) Int. Cl.
- *G01N 33/00* (2006.01)
- *F24F 11/00* (2006.01)
- *G01N 27/66* (2006.01)
- *G01N 1/22* (2006.01)

(52) U.S. Cl.
CPC ...... *G01N 33/0054* (2013.01); *F24F 11/0017* (2013.01); *G01N 1/2226* (2013.01); *G01N 27/66* (2013.01); *F24F 2011/0032* (2013.01); *Y02B 30/78* (2013.01)

(58) Field of Classification Search
CPC ....... G01N 33/0054; G01N 2001/2244; G01N 1/2226; F24F 11/0017
See application file for complete search history.

(56) References Cited

U.S. PATENT DOCUMENTS

| | | | |
|---|---|---|---|
| 4,365,590 A | 12/1982 | Ruggieri et al. | |
| 4,528,898 A | 7/1985 | Sharp et al. | |
| 4,706,553 A | 11/1987 | Sharp et al. | |
| 4,773,311 A | 9/1988 | Sharp | |
| 4,893,551 A | 1/1990 | Sharp | |
| 5,117,746 A | 6/1992 | Sharp | |
| 5,240,455 A | 8/1993 | Sharp | |
| 5,292,280 A | 3/1994 | Janu et al. | |
| 5,304,093 A | 4/1994 | Sharp et al. | |
| 5,385,505 A | 1/1995 | Sharp et al. | |
| 5,406,073 A | 4/1995 | Sharp et al. | |
| 5,435,779 A | 7/1995 | Sharp et al. | |
| 5,545,086 A | 8/1996 | Sharp et al. | |
| 5,865,144 A | 2/1999 | Semenuk | |
| 6,125,710 A | 10/2000 | Sharp | |
| 6,126,710 A | 10/2000 | Futterer | |
| 6,137,403 A | 10/2000 | Desrochers et al. | |
| 6,241,950 B1 | 6/2001 | Veelenturf et al. | |
| 6,252,689 B1 | 6/2001 | Sharp | |

(Continued)

OTHER PUBLICATIONS

The PID Handbook: Theory and Applications of Direct-Reading Photoionization Detectors. RAE Systems. Jan. 1, 2013. Accessed online on Oct. 16, 2016 <http://raesystems.com/customer-care/resource-center/pid-handbook>.*

(Continued)

*Primary Examiner* — Lisa Caputo
*Assistant Examiner* — Punam Roy
(74) *Attorney, Agent, or Firm* — Daly, Crowley Mofford & Durkee, LLP

(57) ABSTRACT

Methods and apparatus for providing an air sampling system with first and second PID sensors to discriminate ammonia measurements. In one embodiment, air samples are taken from a vivarium environment to determine ammonia levels for controlling air flow to the vivarium.

14 Claims, 9 Drawing Sheets

(56) References Cited

U.S. PATENT DOCUMENTS

| | | | |
|---|---|---|---|
| 6,425,297 | B1 | 7/2002 | Sharp |
| 6,609,967 | B2 | 8/2003 | Sharp et al. |
| 6,790,136 | B2 | 9/2004 | Sharp et al. |
| 7,216,556 | B2 | 5/2007 | Desrochers et al. |
| 7,302,313 | B2 | 11/2007 | Sharp et al. |
| 7,360,461 | B2 | 4/2008 | Desrochers et al. |
| 7,389,158 | B2 | 6/2008 | Desrochers et al. |
| 7,389,704 | B2 | 6/2008 | Desrochers et al. |
| 7,415,901 | B2 | 8/2008 | Desrochers et al. |
| 7,421,911 | B2 | 9/2008 | Desrochers et al. |
| 7,527,020 | B2 | 5/2009 | Conger et al. |
| 8,147,302 | B2 | 4/2012 | Desrochers et al. |
| 2003/0137306 | A1 | 7/2003 | Dolgov et al. |
| 2012/0097753 | A1* | 4/2012 | Kelly ................ A61L 9/14 239/6 |

OTHER PUBLICATIONS

Supelco. PID Lamps, Product Specification. T496088A. Sigma-Aldrich Co. 1996. Accessed online at <https://www.sigmaaldrich.com/Graphics/Supelco/objects/4800/4767.pdf> on Feb. 3, 2017.*

* cited by examiner

Table 1

| Actual Concentration | PID with 10.6eV Lamp | | PID with 9.8eV Lamp | |
|---|---|---|---|---|
| | Response Factor | Response (as isobutylene) | Response Factor | Response (as isobutylene) |
| Beta-Pinene | 1 ppm | 0.4 | 2.5 ppm | 0.4 | 2.5 ppm |
| Ammonia | 12ppm | 9.4 | 1.28 ppm | No Response | 0 ppm |

Total Response: 3.78 ppm 2.5 ppm

Differential PID Measurement: 1.28ppm as Isobutylene

*FIG. 7A*

Table 2

| Compound | Compound Ionization Potential (IP) | Health Limit (ppm) | 10.6eV PID Response Factor (RF) | Likely to originate within animal Room? |
|---|---|---|---|---|
| Ethyl Alcohol | 10.47 | 1000 | 10.02 | No |
| Hydrogen Sulfide | 10.46 | 10 | 3.2 | Yes |
| n-Pentane | 10.35 | 1000 | 8.4 | No |
| Ethyl Acrylate | 10.3 | 25 | 2.3 | No |
| Propylene Oxide | 10.22 | 100 | 6.5 | No |
| Ammonia | 10.2 | 25 | 9.4 | Yes |
| Propyl Alcohol | 10.2 | 200 | 5.7 | No |
| Ethyl Acetate | 10.1 | 400 | 4.2 | No |
| Carbon Disulfide | 10.07 | 20 | 1.2 | No |
| Propyl Acetate | 10.04 | 200 | 3.5 | No |
| Butyl Acetate | 10 | 150 | 2.4 | No |
| Dichloroethylene | 10 | 5 | 0.82 | No |
| Isopropyl Acetate | 9.99 | 250 | 2.6 | No |
| Methyl Acrylate | 9.9 | 10 | 3.4 | No |
| Isooctane | 9.86 | none | 1.2 | No |
| Cyclohexane | 9.86 | 300 | 1.4 | No |
| Octane | 9.82 | 300 | 1.8 | No |

Range of compounds a dual PID measurement responds to using a 10.6 eV PID and a 10.0eV PID Added range of compounds a dual PID measurement responds to using a 10.6 eV PID and a 9.8eV PID

FIG. 7B

AIR SAMPLING SYSTEM PROVIDING COMPOUND DISCRIMINATION VIA COMPARATIVE PID APPROACH

CROSS REFERENCE TO RELATED APPLICATIONS

Not Applicable.

STATEMENT REGARDING FEDERALLY SPONSORED RESEARCH

Not Applicable.

BACKGROUND OF THE INVENTION

As is known in the art, there are various applications where an air quality or environmental air measurement system will be utilized to sense one or more indoor air quality parameters for purposes of monitoring and or providing signals for regulating environmental conditions within a building. For example, air measurement systems may be used to monitor air quality parameters including volatile organic compounds (VOCs), as well as inorganic compounds, in order to determine if parameter concentrations are within health or comfort guidelines.

It may be desirable to conduct such measurements on a continuous basis for multiple locations throughout the building or facility, especially in critical environments where specific airborne contaminants or classes of contaminant are expected to accumulate that may have undesirable affects on occupant health or comfort. In order to accomplish this, sensors have been applied using two conventional approaches to monitor the building locations of interest. This includes either the application of discrete sensors installed within each building location, or the use of a centralized monitoring approach, in which a single suite of one or more sensors is installed to sense a plurality of locations using what is generally referred to as a multipoint air sampling system. Considerations that are driving decision makers to increasingly choose multipoint air sampling approaches versus the use of discrete sensors installed within the sensed location concerns factors such as: the ease of implementation, better measurement accuracy, ease of sensor maintenance, and lower initial sensor cost as well as replacement sensor cost over the discrete sensor approach.

For one class of these multipoint air sampling systems, multiple tubes may be used to bring air samples from multiple locations to a centralized sensor(s). Centrally located air switches and/or solenoid valves may be used in this approach to sequentially switch the air from these locations through the different tubes to the sensor to measure the air from the multiple remote locations. These octopus-like systems, which are sometimes known as star-configured or home run systems, use considerable amounts of tubing, but can still be more effective than the discrete sensor approach. An example of such a star-configured system is described in U.S. Pat. No. 6,241,950, which is incorporated herein by reference.

Other types of systems known in the art of air monitoring include those that are designed to monitor refrigerants and other toxic gases, which also are star-configured systems. For example, refrigerant monitoring systems can often use a single expensive non-dispersive infrared (NDIR) sensor to cost-effectively monitor multiple locations for refrigerant leaks, which is far more cost effective than deploying a discrete NDIR sensor per monitored location. However, these sensors tend to work best when detecting parameters against toxic limit values (TLVs), given the accuracy issues that can arise due to sensor fouling.

Another multipoint sampling system known as a networked air sampling system uses a central. 'backbone' tube with branches extending to various locations forming a bus-configured or tree-like approach similar to the configuration of a data network. Air solenoids are typically remotely located proximate to the multiple sampling locations. Networked air sampling systems can also include remote and/or multiple-location air sampling through a tube or pipe for sampling locations in a building, outdoor air or ambient sampling, and sampling in smokestacks and exhaust air stacks. An exemplary networked air sampling system is described in U.S. Pat. No. 6,125,710, which is incorporated herein by reference.

Multipoint sampling systems may be applied to monitor a wide range of locations throughout a building, including any kinds of rooms, hallways, lobbies, interstitial spaces, penthouses, outdoor locations, and any number of locations within ductwork, plenums, and air handlers.

A sensor that may be utilized within a multipoint air sampling system includes as photoionization detector or PID, which is a sensor technology known to those experienced in the art of environmental monitoring as a device which can be used to perform a broad measurement of volatile organic compounds, as well as certain non-volatile organic compounds. PID technology may range in cost from a few hundred dollars to even several thousand dollars per sensor, yet it can be cost effective when used multipoint air sampling systems, as the cost of the sensor is divided among the number of locations sensed by the system. Conversely, PIDs are rarely applied as discrete sensors installed within each location within a building, due to initial sensor costs and maintenance. PIDs can be utilized within hand-held instruments, such as for example various models of the ppbRAE, manufactured by RAE Systems Inc., along with various models made by other manufacturers, including but not limited to: Baseline-MOCON, Inc. Photovac-Inficon, inc., RKI Instruments, etc.

Rather than provide continuous monitoring, these hand-held instruments are designed to perform spot checking and general environmental survey work within a facility or, since they are portable, even in locations outside of a facility. These handheld instruments are often utilized by Environmental Health and Safety (EH&S), facilities personnel, and other facility staff, and these instruments usually have some level of data logging capability, but they do not lend themselves to being permanently installed in order to provide continuous monitoring or to provide signals for purposes of adjusting ventilation based on air quality levels. Also, the PIDs designed for handheld units generally require frequent calibration, and are therefore not practical for continuous use.

One characteristic of a photoionization detector is that it is capable of providing a signal that is simultaneously responsive to multiple compounds. This is based on the way in which these sensors provide detection of compounds, whereby the PID will respond to compounds that have an ionization potential less than or equal to that supplied by the detector's ionization source, which is usually an ultraviolet lamp. Photoionization occurs when a molecule absorbs a photon of energy at a sufficient level to release an electron to create a positive ion. This will occur when the ionization potential of the molecule in electron volts (eV) is less than the energy of the photon. As a compound is ionized by a PID lamp, electron flow is measured as an electrical current that is setup in the sensor electrode, and this current is proportional to the concentration of the gas that has been ionized. Because different compounds can be ionized at a given time, the sensor will be responsive to concentrations of multiple compounds.

Generally, the gases which may be sensed by a PID are those that have an ionization potential that is less than the ionization energy of the PID lamp. Common lamp energy levels available in PIDs include but are not limited to: 11.7 eV, 10.6 eV, 10.0 eV, and 9.6 eV. Therefore, as an example, a PID having a 10.6 eV lamp is capable of detecting acetone, which is a compound having an ionization potential (IP) of 9.69 eV yet, that PID with the same lamp will not detect chlorine, which has an IP of 11.48 eV, and therefore will not be ionized by a 10.6 eV lamp.

Because of the ability of a PID to provide a signal that is responsive to multiple compounds, it has been utilized extensively over recent years within a network air sampling system like that described by U.S. Pat. No. 6,125,710, which is also known commercially as the OptiNet system, produced by Aircuity Inc. The sensor responsiveness to many VOCs and certain no makes it quite useful as a device for providing measurements that can serve as general indications of IEQ, as well as in rendering a signal that can be used by a ventilation control system, such as that found in a laboratory, vivarium, general office space, and other environments. The application of controlling ventilation as a function of contaminant levels within a sensed space is generally known to those knowledgeable in the art of ventilation controls as Demand Control Ventilation, or DCV. As an example, U.S. Pat. No. 8,147,302 B2, which is incorporated herein by reference, describes an exemplary embodiment of how to form a DCV signal to control ventilation levels in a laboratory by way of making a differential measurement of air contaminants, and an excellent approach for making such measurements incorporates a PID sensor. In applications such as this, the broad sensing capabilities of the PID sensor is very desirable since, especially in lab environments, there are potentially hundreds of compounds that need to be detected in order to safely maintain ventilation levels as a part of the DCV strategy.

One motivation for this and other DCV methods is to reduce ventilation rates in order to realize energy savings, by reducing fan energy consumption and the costs associated with heating, cooling, and humidification of air serving the sensed environment. Energy usage relating to ventilation represents one of the most significant operating costs for commercial buildings and, increasingly DCV is being adopted as a leading initiative for facility energy retrofits. The energy efficiency opportunity associated with these programs is so significant that gas and electric utilities are regularly paying incentives to help find significant costs in these retrofits. However, ventilation reductions via DCV must be done in a manner that does not compromise the health and safety of occupants. Within research labs and other similar environments, herein referred to as critical environments, the energy savings opportunity afforded by ventilation reductions is potentially enormous, given that these types of spaces have historically been operated in a substantially over-ventilated manner. From an energy use standpoint, this is compounded by the fact that the air handling or fan systems supplying ventilation to critical spaces are usually designed as "single pass" or 100% outside air systems. This means that for every cubic foot per minute (CFM) of air supplied to these spaces, a matching CFM of outside air must be heated, cooled, or humidified. This is different from conventional recirculating air handling systems used in general commercial office buildings, which can often operate on a fraction of the outside air percentage.

Critical environments have been historically heavily over-ventilated due to many factors including conservative designs and initial designs which provided high ventilation rates in order to satisfy thermal loads which are now no longer present, due to the use of more energy efficient equipment, including more efficient lighting, LCD monitors instead of CRT's, and more efficient refrigerators and freezers used in these spaces. Also, today's laboratories, especially in the life sciences, operate with fewer fume hoods due to the increasing use of microchemistry, where chemicals are used in minute quantities not requiring a fume hood, and computational chemistry; and this helps to drive required ventilation rates lower. Further, AIHA/ANSI Z9.5 laboratory ventilation standards have reduced fume hood minimum flow rate recommendations for variable air volume fume hoods. In addition, the application of a DCV strategy to vary ventilation rates in these critical spaces has only been a trend over recent years given the introduction of technologies such as that described within the teachings of U.S. Pat. No. 8,147,302.

The recent trend to lower ventilation rates in critical environments, has been to reduce air change rates (ACH) in labs from previous designs having fixed values of as much as 12 or more ACH to (using DCV) levels as low as 4 ACH during occupied hours and as low as 2 ACH during unoccupied hours. Such measures can result in ventilation energy reductions by a factor of 3 or more, without compromising occupant health and safety. As mentioned previously, the use of a PID is valuable to these DCV applications, given its broad sensing capabilities, which allows it to detect most of the compounds of interest that occupants may be exposed to in the event of a chemical spill or fugitive emission. In the event of a spill, fugitive emission, or some other source of elevated contaminant levels, the multipoint sampling system monitoring the lab environment via the PID sensor will increase the ventilation or DCV signal provided to the ventilation control system, thus increasing the lab ACH in order to properly dilute the contaminant levels. Under such events, it is common for ventilation rates to be temporarily increased to 12 or more ACH, until contaminant levels in the monitored space subside.

Vivariums or animal holding rooms (also known as laboratory animal facilities, animal rooms, barrier facilities, and other names which are well known to those experienced in the art of managing facilities designed to hold animals) are another type of critical environment which use large amounts of ventilation energy. Generally, vivariums can vary in design based on the types of animals that are to be housed, which can include species of rodents, reptiles, birds, non-human primates, and even fish and other animals, but most commonly house rodents, such as rats and mice. Animal rooms are commonly found in most research facilities, including but not limited to pharmaceutical and higher education facilities, where biomedical and psychological research is conducted. In biomedical research, animals are used extensively in research and development of drugs and treatments, including discovery, safety testing, clinical trials, and even during the drug manufacturing stage. Mice and rats are often used because their immunological responses and genetic structures closely resemble that of humans, and this is very important to disease research and drug development. In fact the pharmaceutical industry is especially dependent on animal research for product development, and this has resulted in an industry where animals, such as rats and mice, are genetically bread for specific research requirements.

Because of the time and effort invested into these animals and the critical role that they play in research, they can be valuable assets. As such, peat care is taken to ensure that the environment that they are housed in is a healthy one, especially in terms of IEQ, light levels, temperature, and relative humidity.

When rodents are housed, they are usually placed within individual bins or cages, and these cages are often combined within a rack comprising multiple cages. Examples of cages and cage rack systems include but are not limited to those disclosed in U.S. Pat. No. 5,865,144, U.S. Pat. No. 4,365,590, and U.S. Pat. No. 7,527,020, all of which are incorporated herein. Each cage is typically capable of containing 1 or 2 rats or up to 4 or 5 mice; and a rack, which will usually be on wheels may comprise 100 or more cages stacked in vertical and horizontal directions. Thus, the cage rack approach provides an effective way to house many animals in a relatively small space. Also, it is very common for animal holding rooms to contain numerous cages; and therefore these rooms, at any one time may contain hundreds and in some cases, thousands, of animals. A few of the more common manufacturers of these cage rack systems include: Animal Care Systems Inc., Allentown Inc., Tecniplast S.p.A., and Arrowmight, Inc. Those versed in the art of housing animals in vivarium facilities, will recognize that the cage in which the animal is housed is typically referred to as the primary space or microenvironment, while the room in which the cage or cage rack is placed is typically called the secondary space or macroenvironement.

In one known cage rack system, the individual cages within the cage rack are in communication with the secondary environment such that any gases or vapors emanating from within the cage are allowed to flow or diffuse into the secondary space. In this embodiment, the cage rack system is said to be non-ventilated, or un-ventilated. Also, non ventilated cage rack systems are in bidirectional vapor communication with the secondary space, in that, vapor contaminants in the secondary space will freely diffuse into the individual cages. In another conventional cage rack system, the individual cages within the cage rack are connected to an exhaust duct, which is used to continuously exhaust a finite amount of airflow from the cages, thus preventing vapors from the cages from flowing into the secondary space. In this embodiment, the cage rack system is said to be ventilated. There are other variations of ventilated cage racks that may include supply flow or a combination of supply and exhaust flow to the cage rack system but, the most common of the ventilated cage rack systems by far typically are those which are provided with exhaust airflow. Also, when only exhaust airflow is provided to the cage rack systems, the cages will be at a slightly negative pressure with respect to the secondary space surroundings and, thus, air will generally flow from the secondary space or environment to the cages. Therefore, regardless of whether the cage rack system is ventilated or non-ventilated, it is desirable to maintain the quality of the secondary space environment, as it can have direct impact on the health and well being of the animals in their cages.

FIG. 1 is a simplified illustration of some of the equipment and ventilation system components found within a typical animal holding room 115. Usually, especially if mice or other rodents are involved, this includes a cage rack system 111, which contains a plurality of cages 110. Each of the cages 110 provides a microenvironment to protect the animals. The cage rack system 111 can be on wheels 114 for mobility to enable the entire rack system 111 to be moved with ease for cleaning purposes as well as to enable the rack system 111 to be easily transported to another location. If the cage rack system is a ventilated one, such as that shown in FIG. 1, it typically at least includes a connection to the exhaust system 107. The exhaust system 107 is actually a plenum connection that will usually connect through manifolded ductwork to an exhaust fan that usually serves a number of rooms.

The ventilated cage rack 111 can use the macroenvironment of the animal holding room 115 as a source of makeup air, so that air flows freely from the surroundings 116 into each cage 110. Alternatively, supply air may be provided to cage rack 111 by way of a localized supply fan 108, which also usually incorporates a filter assembly. This provides airflow to supply the cages 110 through manifold 109. Exhaust air is then carried, through manifold 113 through ductwork connection 112 through airflow control device 104. Ventilation to the macroenvironment is provided via supply air 103 through airflow control device 102 via the supply air plenum 101, which is usually connected to manifolded ductwork to a supply fan that usually servers multiple rooms in the facility. Air is exhausted from room 115 via exhaust flow control device 105, which is connected to an exhaust fan through 107. In application, the pressurization of space 115 is established based on the difference between the airflow rate supplied via 102 to the space and that exhausted from the space through 105. In addition, any net airflow from the surroundings 116 supplements the exhaust quantity through 105. Therefore, if supply fan 108 is not present, the pressurization of space 115 will be determined based on the difference between the supply air provided via supply flow control device 102 and the sum of the exhaust flows provided via exhaust flow control devices 104 and 105. When the total flow exhausted from environment 116 exceeds that supplied to it (a flow condition known in the art as a negative offset), the space 116 is said to be negatively pressurized. A space that is negatively pressurizes acts to prevent contaminants from migrating beyond room 115 to other rooms or corridors that may surround this space. When a space is set to a negative offset or is negatively pressurized, airflow is allowed to flow from spaces external to room 115 via gaps under the door(s) leading to the space 115.

In other configurations, the total supply flow via 102 will be set higher than the total exhausted from environment 116, and the space 115 is said to be positively pressurized via a positive offset. In this case no air, and therefore no contaminants, will flow from the rooms or corridor external to space 115, but air will instead flow from environment 116 into these surroundings; again through gaps under the door(s) leading to the space 115. In a positively pressurized mode environment 116 will be isolated from its surroundings.

Similar to general research labs, vivariums are usually ventilated with 100% outside air, and they have historically been operated at relatively high air change rates, at levels that can be even higher than that of research labs. Here, it is not uncommon for vivariums to operate at levels of 15 to 20 ACH, or even higher levels. In many cases vivariums used to be designed to operate at sine high air change rates to ensure that worst case thermal loads could be supported due to heat generated by the animals as large numbers of animals are housed. In addition, under this circumstance, given the legacy caging systems, which generally were not ventilated, the odor levels as well as levels of toxins in a holding room could reach unacceptable levels for personnel working in those rooms. However, the increased use of ventilated cage racks has allowed air change rates in the secondary environments to be lowered significantly and, increasingly, demand control ventilation, using the teachings of U.S. Pat. No. 8,147,302 B2, is being applied to vivariums in order to realize significant reductions in energy usage. Given the enormous energy costs associated with running vivarium facilities, there is also an increasing trend to apply DCV even when non ventilated cage racks are in use.

One of the compounds of concern in vivarium applications is the ammonia that is generated as a result of the microbial decomposition of animal wastes. Ammonia concentrations from animal cages tend to increase over time as animal bedding becomes soiled. The rate at which this happens is partially a function of the type of bedding used the amount of waste produced by each animal and environmental conditions, such as relative humidity and temperature. For mice, rats, and other rodents, a variety of different beddings may be used including: hard wood chips, corn cob bedding, pine shavings, cellulose bedding, and many other types of materials, that are chosen based on tradeoffs between bedding cost, the quality of the environment required, and the longevity that a bedding can provide before it needs to be changed. The frequency with which cages need to be changed is a practical issue, as the bedding changing process tends to stress the animals, which may in turn affect their health. Regardless of the bedding used, bedding needs to be changed, and cages cleaned, on a periodic basis, and there is a definite correlation between the ammonia levels emanating from a cage and the cleanliness of the cage environment. Ammonia levels allowed to emanate from cages into the vivarium's secondary space can affect the health and well being of personnel who care for the animals and the ventilation system plays an important role in maintaining the quality of this environment. Moreover, the amount of ammonia production from a typically active unventilated cage rack can easily result in ammonia concentrations within the secondary space that exceed health limits, if that space is not sufficiently ventilated.

The National Institute for Occupational Safety and Health (NIOSH) has set the toxic limit value (TLV) for ammonia as 35 ppm, based on a time weighted average (TWA) exposure of 8 hours. Industry practice has been to keep ammonia concentrations well below the 35 ppm TWA within the vivarium secondary space, while also minimizing the frequency of bedding changes. In addition, chronic occupation exposure to ammonia at concentration even less than the prescribed TLV's has been linked to abnormal respiratory conditions including bronchial hyperresponsiveness, coughing, wheezing, and discomfort.

Before the use of continuous monitoring technologies, such as that described within the teachings of U.S. Pat. No. 6,125,710, the most common ways to provide verification of the secondary space IEQ was to use hand held sensors specific to ammonia, a handheld PID, or to perform air sampling by way of grab sample devices, such as colorimetric gas detection tubes. Those experienced in the art of environmental monitoring will recognize that a colorimetric gas detection tube (a Draeger tube, for example) is a consumable device, that is used once and then disposed of. To provide more sampled data specific to ammonia, handheld electrochemical sensors have been used and can provide fairly accurate measurements over short periods of time. Electrochemical sensors work by using an electrolyte to oxidize or reduce the target compound. The electrochemical reaction produces a current which is measured and is proportional to the concentration of the target gas. These sensors are better suited for use in a handheld device, where they can be frequently calibrated or replaced, given the practical limitations on calibration stability and the useful life of these devices. One characteristic of electrochemical sensors used to detect ammonia is that they have a life expectancy rating in ppm/hours. When exposed to low ammonia concentrations (a few ppm), they can last for many months. However, given, the relatively high levels of ammonia that will be present even in a well-ventilated vivarium, often exceeding 15 ppm, most can only continuously operate accurately for a period of a few days. This is not a problem with the way a handheld instrument is used, however, given that they will only be used for a few hours at a time and, that they can be readily recalibrated between uses.

Alternatively, IEQ verification can also be provided using a handheld PID sensor having an appropriate lamp which is able to ionize ammonia. For example, the ionization potential of ammonia is 10.16 eV so, using a PIT) with a more commonly available 10.6 eV lamp, or even one with an 11.7 eV lamp, provides an effective way to broadly measure for ammonia levels, but it will also be responsive to other compounds in the measured environment. Handheld PIDs are commonly used by EH&S and other professionals for general monitoring of IEQ conditions in any type of facility both fir purposes of routine inspection as well as in response to an event, such as a chemical spill. Because of its broad response and use in detecting many different compounds, a PID is often calibrated on one reference compound and response factors are established to that reference compound for the various compounds to be measured. These response factors do vary with the PID design along with the energy of the lamp. For example, it is common to calibrate a PID sensor on isobutylene and most manufacturers have established a list of compound response factors to this reference compound. Thus, measurements made from a PID calibrated in this way will be in units of isobutylene (often called "as isobutylene"). Using a PID with a 10.66 eV lamp, a common response factor for ammonia includes, but is not limited to, 9.4. This means that when such a PID is exposed to 9.4 ppm of ammonia, its reading will be 1 ppm as isobutylene.

As has been described above, PIDs have found use in multipoint sampling systems (such as the system disclosed in U.S. Pat. No. 8,147,302 B2 and 6,126,710) in order to provide DCV and or IEQ monitoring functions. The sensitivity that these sensors have to many different compounds can be quite beneficial, especially when measuring for a plurality of different compounds. However, the sensor's lack of specificity to certain compounds can at times result in an over response to an IEQ condition, which can represent the condition as being more serious than it really is and, can result in higher ventilation rates than is necessary, as a result of the DCV response to the IEQ condition. For example, in vivariums rats and mice are sometimes provided with softwood bedding (typically aspen shavings) which can emit low levels of beta-pinene. Beta-pinene is detected by PIDs using any of the common lamps including but not limited to: 11.7 eV, 10.6 eV, 10.0 eV, and 9.6 eV. For any of these PID lamp types, beta-pinane has a strong response due to its relatively low ionization potential of approximately 8.0 eV. For example, a typical response factor for this compound when using a 10.6 eV lamp is 0.40. That means that 0.4 ppm of beta-pinene results in a 1 ppm as isobutylene response. Given a typical response factor for ammonia, the presence 0.4 ppm of beta-pinene will appear similar to that of 9.4 ppm of ammonia. However, beta-pinene is not toxic at practical levels that may be seen in such environments yet, its presence can and does usually result in an overestimation of the IEQ levels in these environments; again depending on the type of bedding used. In vivariums, there are a number of relatively benign. "interfering" compounds which will naturally be present due to a combination of bedding materials, the use of cleaning agents, and volatile organic compounds emanating from the animal cages. This includes but is not limited to: dimethyldisulfide, acetone, and various mercaptans.

SUMMARY OF THE INVENTION

The present invention provides methods and apparatus for the discrimination of ammonia and other harmful compounds commonly generated within animal holding rooms, including any combination of micro or macro environments therein, for IEQ) monitoring and or ventilation control purposes. While exemplary embodiments are shown and described in conjunction with animal holding rooms, exemplary embodiments are also applicable to any type of spaces that may be subject to airborne contaminants introduced by animals held within those spaces, or as a result of any combination of cross contamination from other locations in the facility or entrainment of contaminants through the outdoor intakes of the facilities ventilation systems. Other embodiments include applications where ammonia levels not derived from the housing of animals need to be detected.

In one aspect of the invention, a method of providing a discriminating measurement of ammonia along with a limited number of secondary airborne parameters associated with animal waste from an indoor environment comprises: obtaining an air sample by a multipoint air sampling system which contains a representative concentration of ammonia and said other secondary airborne parameters from said environment, measuring said air sample by a higher photonic energy photoionization detector applied within said multipoint air sampling system to create a first photoionization detector signal, measuring said air sample by a lower photonic energy photoionization detector applied within said multipoint air sampling system to create a second photoionization detector signal, and generating a PID) measurement derived from the said second photoionization detector signal and said first photoionization detector signal.

The method can further include one or more of the following features: generating the PID measurement by subtracting the second photoionization detector signal from the first photoionization detector signal, the PID) measurement is proportional to the second photoionization detector signal subtracted from the first photoionization detector signal, the multipoint air sampling system comprises a star configuration system, the multipoint air sampling system comprises a networked air sampling system, the higher photonic energy photoionization detector has a 10.6 eV lamp and the lower photonic energy photoionization detector has a 10.0 eV lamp, the indoor environment is a vivarium, the indoor environment comprises cage racks, the indoor environment is an exhaust duct connected to a cage rack which is monitored by said multipoint sampling system in order to keep track of the environmental conditions of the cages, and/or the PID measurement is used to optimize the cage bedding change schedule.

In another aspect of the invention, an air sampling system comprises: an air sample by a multipoint air sampling system to obtain air samples, a sensor suite including a higher photonic energy photoionization detector to create a first photoionization detector signal and a lower photonic energy photoionization detector to create a second photoionization detector signal, and a processor to generate a PID measurement derived from the said second photoionization detector signal and said first photoionization detector signal to discriminate ammonia.

The system can further include one or more of the following features: the air samples are obtained from a vivarium environment, the PID measurement is used to generate an air flow signal to control air flow to the vivarium environment, the PID measurement is used to derive a schedule to change animal bedding material, and/hr the higher photonic energy photoionization detector has a 10.6 eV lamp and the lower photonic energy photoionization detector has a 10.0 eV lamp.

In a further embodiment of the invention, a method of rendering a DCV signal in order to control the ventilation rate of an environment so as to limit ammonia levels along with a limited number of other pollutants associated with animal waste comprises: using a multipoint air sampling system to extract an air sample from a location associated with ammonia, discriminating a measurement of ammonia using first and second PID sensors, and presenting the DCV signal to air flow controls in order to adjust an air change rate based upon the discriminating ammonia measurement.

The method can further include one or more of the following features: the DCV signal is derived differential sampling from at least two locations, the differential sample is proportional to the PID measurement made on air samples taken from an exhaust air duct leading from said environment minus the dual PID measurement made on air samples taken from the supply air duct leading to said environment, and/or the differential sample is proportional to the PID) measurement made on air samples taken directly from some location within said environment minus the dual PID measurement made on air samples taken from the supply air duct leading to said environment.

BRIEF DESCRIPTION OF THE DRAWINGS

The invention will be more fully understood from the following detailed description taken in conjunction with the accompanying drawings, in which:

FIG. 7A is a tabular representation of PID response to various components;

FIG. 7B is a tabular representation of a list of the range of compounds found in chemical inventories that a PID measurement would be sensitive to that may either likely appear due to outside air entrainment, or will likely originate within an animal room.

DETAILED DESCRIPTION OF THE INVENTION

In general, exemplary embodiments of the invention provide a multipoint air sampling system which utilizes at least two photoionization detectors (PIDs) having lamps which expose the electrodes for each sensor with different light energies or wavelengths in such a way to ensure that one PID is capable of ionizing a broader range of compounds than the other. It is understood that the air sampling system can be provided in any suitable configuration. In an exemplary embodiment, a networked air sampling system can include features described in U.S. Pat. No. 6,125,710 along with the duct probe assembly system described in U.S. Pat. No. 7,421,911 (both of which are herein incorporated by reference) to deliver air samples to the PIDs having different lamp energies. The teachings of U.S. Pat. No. 6,125,710 enable highly accurate measurements to be made with a PID, with minimal tolerance stacking errors between measured locations, which is useful given the comparative function that is performed when measuring contaminant levels. For example, U.S. Pat. No. 6,125,710 involves performing a first measurement of contaminant levels in a room and then subtracting from that measurement a second measurement of contaminant levels from the supply air provided to the room according to the teachings of U.S. Pat. No. 8,147,302 B2.

Figure 1:
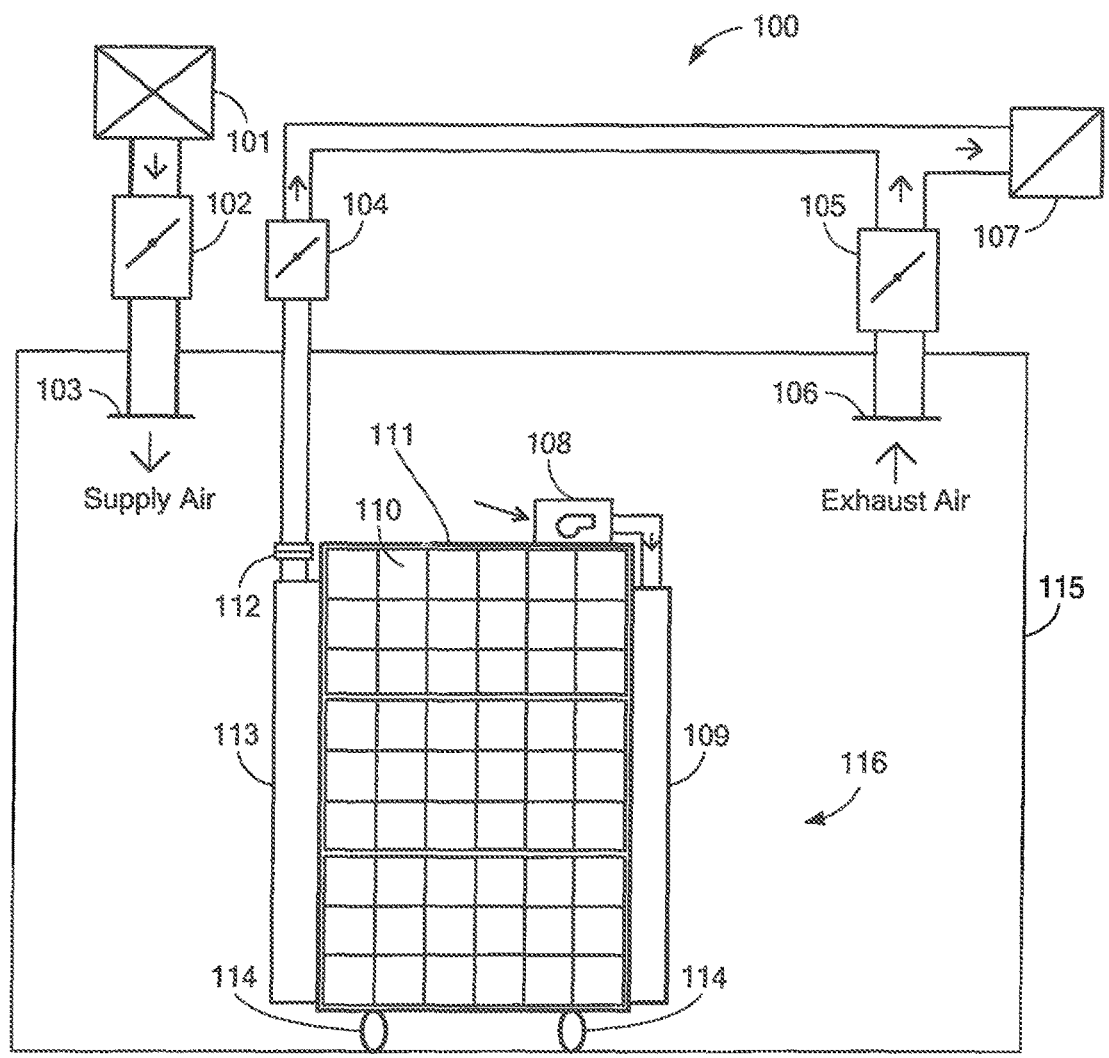
FIG. 1 shows an exemplary prior art ventilation system for an animal holding room.
Figure 2:
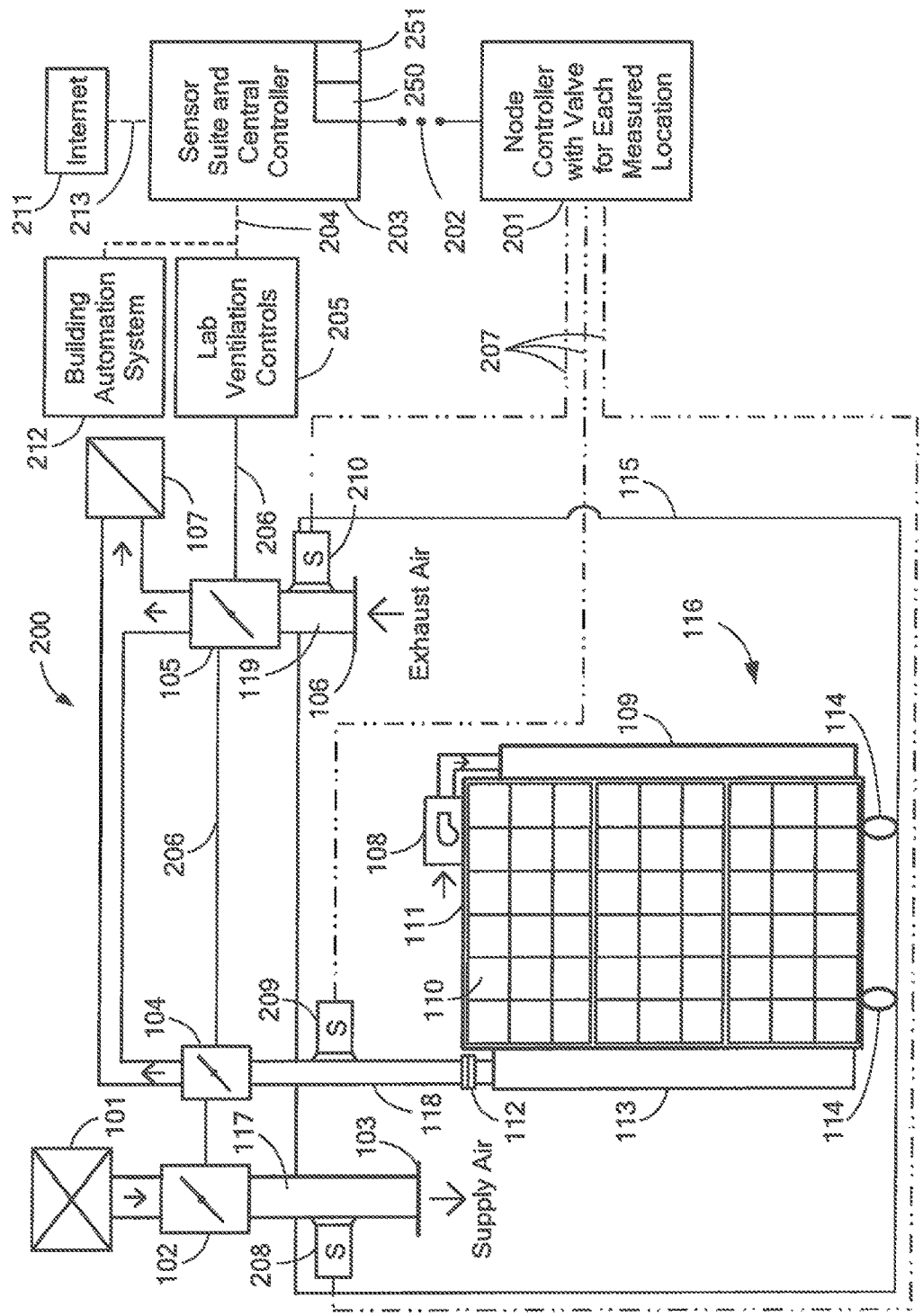
FIG. 2 is a schematic representation of an exemplary networked air sampling system having first and second PID sensors in accordance with exemplary embodiments of the invention.

FIG. 2 shows exemplary networked air sampling system 200 for monitoring a typical animal holding room configuration 100 and provide a DCV signal to the ventilation controls system for that room. The networked air sampling system contains at least two PID sensors 250, 251 for monitoring ammonia along with other compounds, including many TVOCs and other parameters. Other sensors may also be included with the networked air sampling system; such as any combination of a particle counter, carbon monoxide sensor, carbon dioxide sensor, moisture sensor, and other sensors. The illustrated embodiment includes duct probe locations 208, 210 and, optionally, 209. The duct probes provide a way for the networked air sampling system to acquire air samples from supply air duct 117 and exhaust air ducts 118 and 119 using probes, such as those described in U.S. Pat. No. 7,421,911, which is incorporated herein by reference.

In one embodiment, air samples are drawn through structured cable 207, which are sequenced through a node controller 201, conveyed through a common backbone 202, which can be identical or similar to structured cable 207, and sensed via sensor suite 203. An exemplary structured cable 207 and 202 is described in U.S. Pat. No. 7,360,461 B2, which includes tubing that enables air samples to be transported with minimal loss to the properties of interest. One of the properties of interest in this case is the ammonia concentration within the air sample that should not degrade or change, as it is conveyed from probes 208, 209, or 210 through the structured cable 207, the node controller 201, and structured cable 202, to the sensor suite 203. Structured cable 207 and 202 also provide power, control and communications wiring to support the interconnection of the element of this system.

While the sensor suite and central controller 203 are shown as one element in the illustrated embodiment it is understood that the central controller can be separate from the sensor suite and that there may be any practical number of sensor suites operated by the central controller, which is the main CPU or computer that operates the multipoint air sampling system and may also be the device which performs the logic to translate sensed parameter levels into a DCV signal which in turn is communicated to the lab ventilation controls 205. The communication between the central controller 203 and the lab ventilation controls 205 is accomplished though connection 204, which includes but is not limited to any type of network connection or hard wired analog signals.

In one embodiment, communication over connection 204 is achieved by way of a BACnet protocol, which is a well known standard for the HVAC industry. Central controller 203 may also be connected to a building automation system 212, or BAS, so that what is sensed at each location 208, 209, and 210 may be viewed or data logged by the BAS. In some cases, the BAS 212 can also be used to facilitate communications over network 204 between central controller 203 and lab ventilation controls 205. In other embodiments, the lab ventilation controls 205 will be a part of the BAS, which directly communicates to flow controls 105, 104, and 102 over connection 206.

In addition, exemplary configuration 200 will include a connection 213 to the internet which enables central controller 203 to communicate the parameter values sensed via sample locations 210, 209, and 208 to a remote server or data center, which allows this data to be analyzed and stored. This allows software information services to be provided on this data, including but not limited to data graphing and exporting capabilities, event notification services, reporting, data mining, and data visualization services such as dashboarding functionality. Another feature supported via the internet connection 213 is something known in the art as proactive monitoring services, whereby the integrity of the network air sampling system components including but not limited to sensor suite and central controller 203, node controller 201, and duct probes 210, 209, and 208 can be continuously or periodically monitored to ensure that the system and its components are functioning properly. This proactive monitoring capability may be provided via manual data inspection by remote service personal or it may be accomplish through software that has been configured to analyze the data from this system in order to identify performance issues. Proactive monitoring may also be accomplished via any combination of manual and automated analysis methods.

One issue with any multipoint sampling system (not just that described in configuration 200) is that any of the sensors incorporated to provide parameter sensing can malfunction. For example, a sensor such as a PID sensor or other sensor can drift or catastrophically fail due to environmental exposure, thermal degradation, fouling, electronic failure, and many other possible issues. This may occur regardless of the sensor's age, or the technology used for sensing and, therefore, the proactive monitoring function provides a distinct advantage over air monitoring approaches which do not incorporate this function as it provides a method to identify performance issues which, as they are identified may be addressed, thereby ensuring continuous operation of the multipoint sampling system while minimizing down time.

Figure 3:
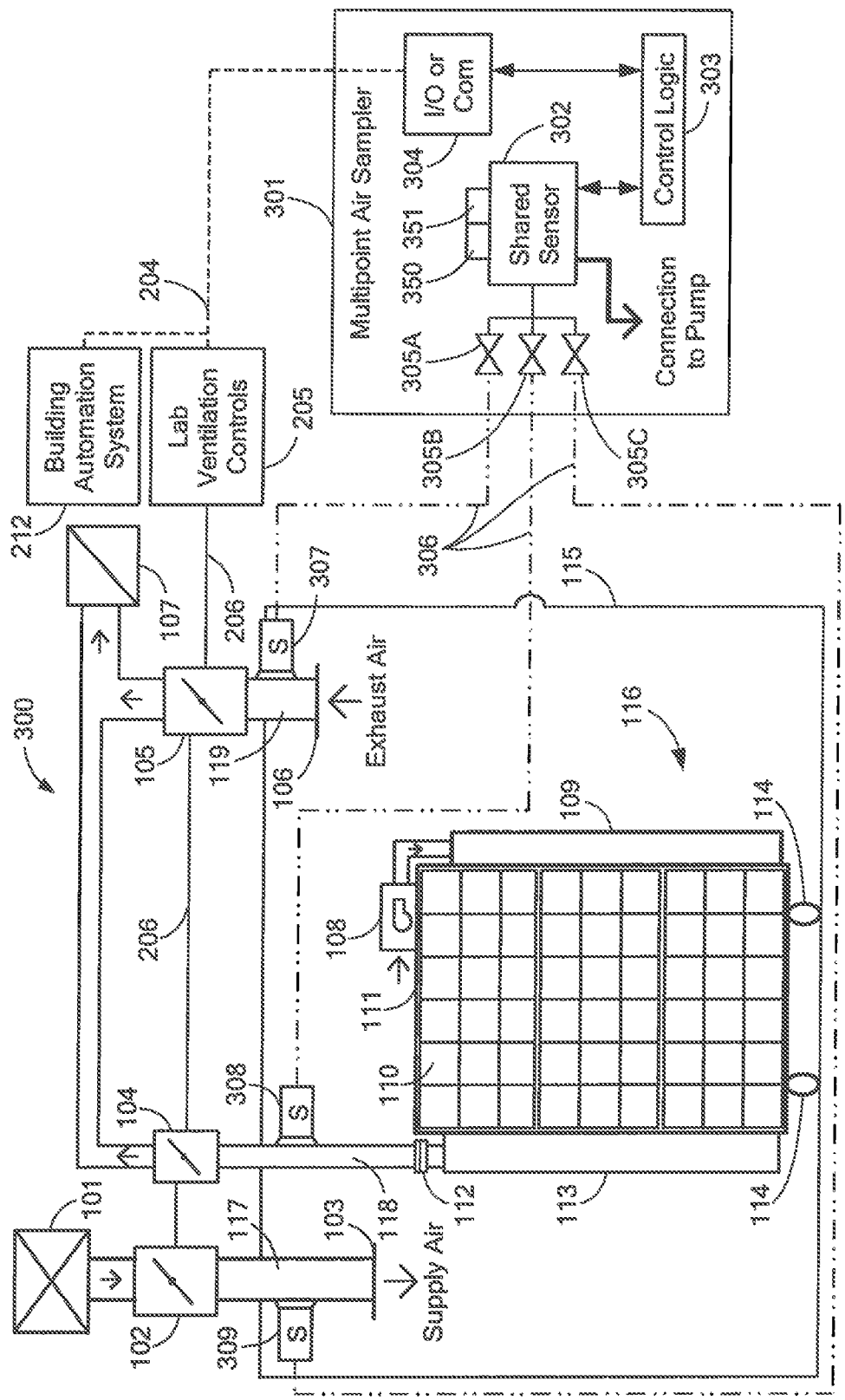
FIG. 3 is a schematic representation of an exemplary star configured multiple point air sampling system having first and second PID sensors in accordance with exemplary embodiments of the invention.

FIG. 3 illustrates an alternate embodiment of a monitoring animal holding room configuration 100 by way of a star configured multiple point air sampling system having at least first and second PIDs 350, 351. The configuration 300 includes a multipoint air sampler 301, which could be a star configured multipoint air sampling system like that described in U.S. Pat. No. 6,241,950, it could be a multipoint air sampling system like that described in U.S. Pat. No. 5,292,280, or it could be any multipoint refrigerant or toxic gas monitor adapted for this purpose. Multipoint air sampler 301 incorporates sampling valves 305A, 305B, and 305C, used to take samples from sampling locations 307, 308, and 309, respectively, using tubing 306. Tubing 306 includes any commercially available tubing, including but not limited to general grade polyethylene or high density polyethylene HDPE tubing often used as pneumatic tubing in HVAC and other systems, as well as tubing made of materials that will perform better than HDPE when sampling adsorptive compounds such as ammonia. This includes many tubings which are readily commercially available such as tubing made of Teflon, polyvinylidene fluoride and other fluoropolymers. In other embodiments, structured cable 207 is preferred.

The multipoint air sampler 301 can communicate directly to the lab ventilation controls 205 or to the building automation system 212 but, unlike the central controller 203 in the exemplary configuration 200, the products available which may be used as multipoint air sampler 301, are very limited in their programmability and logic flexibility, which transfers the burden of the ventilation control sequence to the BAS 212 or to the lab ventilation controls 205.

In addition, configurations such as 300 which incorporate star configured multipoint sampling systems tend to use a lot of tubing 306. This is due to the fact that multipoint air sampler 301 contains the one or more sensors 302 along with the air sampling valves 305 for each monitored location. Of the components, the shared sensors 302 are relatively expensive compared to the costs of the other components within the air sampling system. Also, it is desirable to minimize the number of midpoint air samplers 301 per facility, given the maintenance costs associated with sensor calibration. Therefore, what tends to happen when these systems, such as 301, are deployed is that they are applied in such a way as to ensure a maximum number of sampled locations are served per multipoint air sampler 301. In practice, therefore, each multipoint air sampler 301 would be applied to as many animal room configurations 100 as possible (along with other spaces that may simultaneously need to be monitored), which means that many tubes 306 have to be run from these monitoring points back to a common location where the multipoint air sampler 301 has been installed. This can result in hundreds or even thousands of feet of tubing 306 being required and, especially if higher grade fluoropolymer tubing is used it can become expensive. Alternatively, with the exemplary configuration 200, the different sampling points (208, 209, 210) for each animal holding room configuration 100 is typically served by a single node controller 201 which is placed in proximity to the monitored locations and thus, the amount of tubing within structured cable 207 required in these configurations is substantially less than the tubing 306 utilized within the configuration 300.

In practice multiple node controllers 201 are utilized per sensor suite 203, allowing for a more distributed approach and more efficient use of tubing. Nevertheless, the teachings of this invention provide great benefit to any type of multipoint sampling system, including the networked air sampling system described within configuration 200 as well as the multipoint air sampler described within configuration 300.

It is understood that embodiments of the invention are not limited to environments of the configuration described above but that what has been described in that illustration is an example of how a micro and macro environment is often established for the animals to be housed. Embodiments of the invention apply equally to any variation of animal housing environment, including but not limited to ones with any number of animal cage racks, environments without cage racks, and environments that employ other methods of housing animals other than a cage rack approach. One example of an environment which may not incorporate cages or cage racks includes rooms and facilities designed for non-human primates. These types of spaces may or may not include a micro-environment and are designed to house a diverse list of animals including but not limited to: many species of monkeys (old world, new world), lower primates, lesser apes, great apes, and other primates. The benefits also apply to less critical animal holding rooms and even general spaces where animals may be housed including but not limited to general lab space that may contain animals, commercial, and even domestic environments. For example, the benefits air monitoring in accordance with the invention are applicable for use in environments provided by pet suppliers in retail establishments and especially in distribution warehouses where large numbers of animals are to be housed.

It is also understood that the teachings of the invention apply to the monitoring and control of ventilation in environments that are occupied substantially by humans where sources of ammonia and related contaminants are generated from human processes or waste, where it may be beneficial to use the apparatus and methods of this invention to perform IEQ monitoring and or ventilation control while providing specificity to ammonia.

Exemplary embodiments of the invention provide a multipoint sampling system which incorporates two or more PIDs to provide discriminating measurements of ammonia along with other compounds associated with animal waste that may accumulate within the sensed environment.

In one embodiment, a multipoint air sampling system utilizes two PIDs to provide a sensor difference measurement for each air sample, involving a first PID which is configured with a first ionization source at one level of ionization energy and a second PID configured with a second ionization source that provides a lower ionization energy than said first ionization source. In this embodiment, the dual PID measurement provides a discriminating measurement of ammonia along with other compounds associated with animal waste by subtracting the measurement made on the sample using the second PID from that made using the first PID.

A dual PID measurement is applied to one sampled location either in the room or within an exhaust duct leading from the room to establish an absolute measurement of the ammonia and other related contaminants in the measured environment. In this embodiment, it is assumed that what is discriminated by the dual PID measurement will correlate to contaminants generated within the animal room. As an example of how this applies to the animal room configuration 200, this embodiment would apply a dual PID 250, 251 measurement to samples taken from sampled location 210 within the room's exhaust air to establish a measurement that is representative of ammonia along with other compounds associated with animal waste that may accumulate within the room 115.

To better appreciate the significance of the dual PID measurement approach, Table 1 in FIG. 7A illustrates a condition where the measured location contains 12 ppm of ammonia and 1 ppm of beta-pinene, which is another compound that is commonly found within an animal holding room, as discussed previously. In this example, the higher energy PID utilizes a 10.6 eV lamp, and the lower energy PID utilizes a 9.8 eV lamp, and it is assumed that both PIDs are calibrated to isobutylene. Additionally, Table 1 shows that, in this example, both the 10.6 eV PID and the 9.8 eV PID have substantially the same response factor to beta-pinene which, in this case is a value of 0.4. That means that in the presence of 0.4 ppm of beta-pinene, both the 10.6 eV PID and the 9.8 eV PID will exhibit a reading of 1 ppm, as isobutylene. This means that, in the presence of 1 ppm of beta-pinene the partial response of each PID to this compound will be 2.5 ppm as isobutylene. Additionally, as seen from Table 1, the 10.6 eV PID's response factor to ammonia in this case will be 9.4; meaning that in the presence of 12 ppm of ammonia, that sensor will exhibit a partial response to ammonia equivalent to 1.28 ppm as isobutylene. Therefore, the combined response of the 10.6 eV PID response to the stated levels of ammonia and beta-pinene is 3.78 ppm as isobutylene. Also, note that from Table 1, the response factor of the 9.8 eV PID is essentially infinite; that is there is no response to ammonia exhibited from this sensor. Therefore, in this scenario, the only response exhibited by the 9.8 eV PID is that to beta-pinene, or 2.5 ppm as isobutylene. Once again, the dual PID method will subtract the 9.8 eV PID response from that of the 10.6 eV PID, resulting in a net reading of 3.78 ppm-2.5 ppm, or 1.28 ppm as isobutylene. In practice, the net value is converted to the concentration of the compound of interest which, in this case is ammonia, by using the response factor of the higher energy PID (the 10.6 eV PID) to ammonia, resulting in a net reading of 12 ppm as ammonia. Thus, the dual PID measurement in this case results in an ammonia specific measurement, and such an approach can be applied to either configuration 200 via sensor suite and central controller 203 or configuration 300, via multipoint air sampler 301 in order to establish a measurement of ammonia levels within the space 116 which can be used to provided IEQ information for historical trending purposes, for example, as well as to formulate a DCV signal which can be used to adjust the ventilation rate in the room 115 using lab controller 105. Here, the ability to reject the beta-pinene levels from the measurement is significant, given the relatively high sensitivity that a PID has to this compound and the fact that it will generally only exist in low levels within an animal holding space that are not toxic, but yet would result in an unnecessarily high measurement if only a single PID were used, and if this signal is used for DCV purposes, it results in an overestimation of IEQ levels in the space, that also would result in higher than necessary ventilation commands to the lab controller 105, thus resulting in energy waste.

Figure 4:
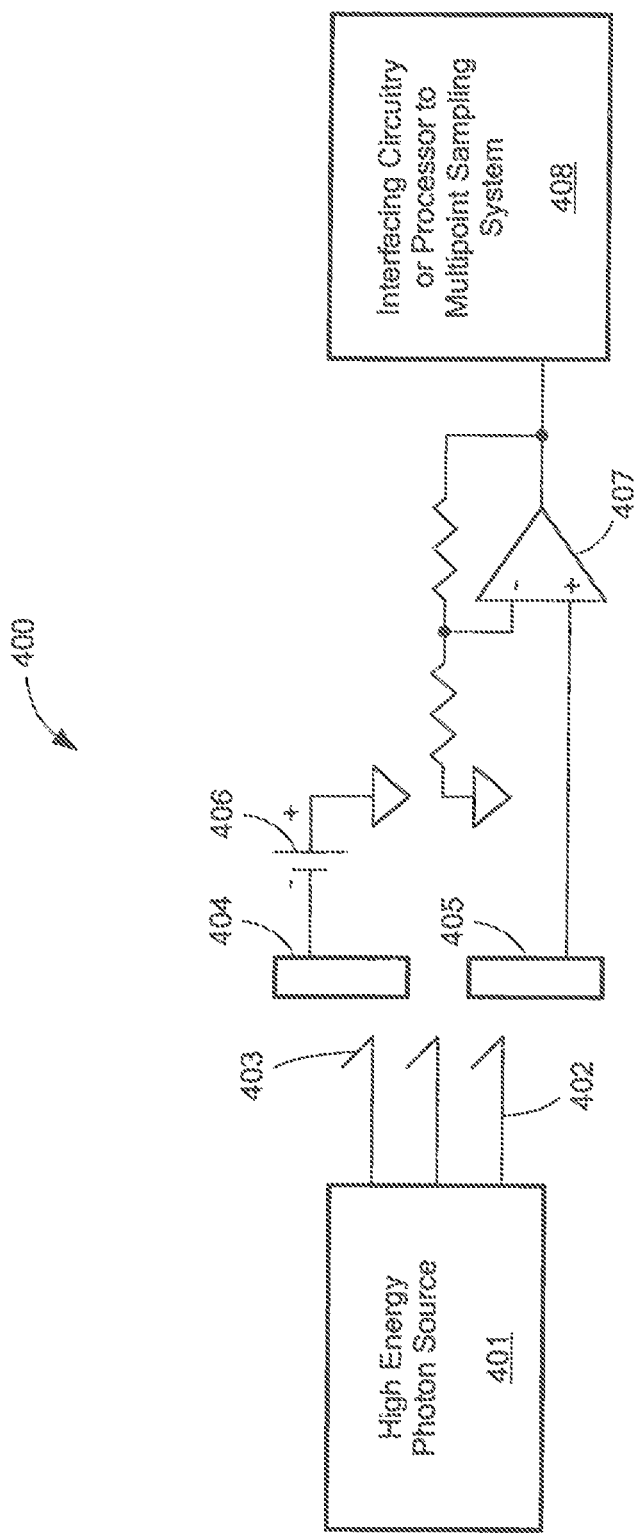
FIG. 4 is a schematic representation of an exemplary PID and components.

FIG. 4 is a generalized illustration of the basic components to a PID. This at least includes a high energy photon or light source 401 (such as an ultraviolet or UV lamp), an ionization chamber 403, and a sensing electrode 404 and 405 along with sensing instrumentation 407. It is understood that numerous PID configurations exist and there may be variations on the combination of PID light sources to electrodes. An example of a PID design is described within U.S. Pat. App. No, 2003/0137306 A1, which is incorporated herein by reference. In exemplary embodiments of the invention, the application of two or more PIDs for discriminating ammonia and other compounds associated with animal waste implies that there are at least two or more high energy photon sources and any combination of electrodes and sensing instrumentation utilized by the multipoint air sampling system.

Figure 5:
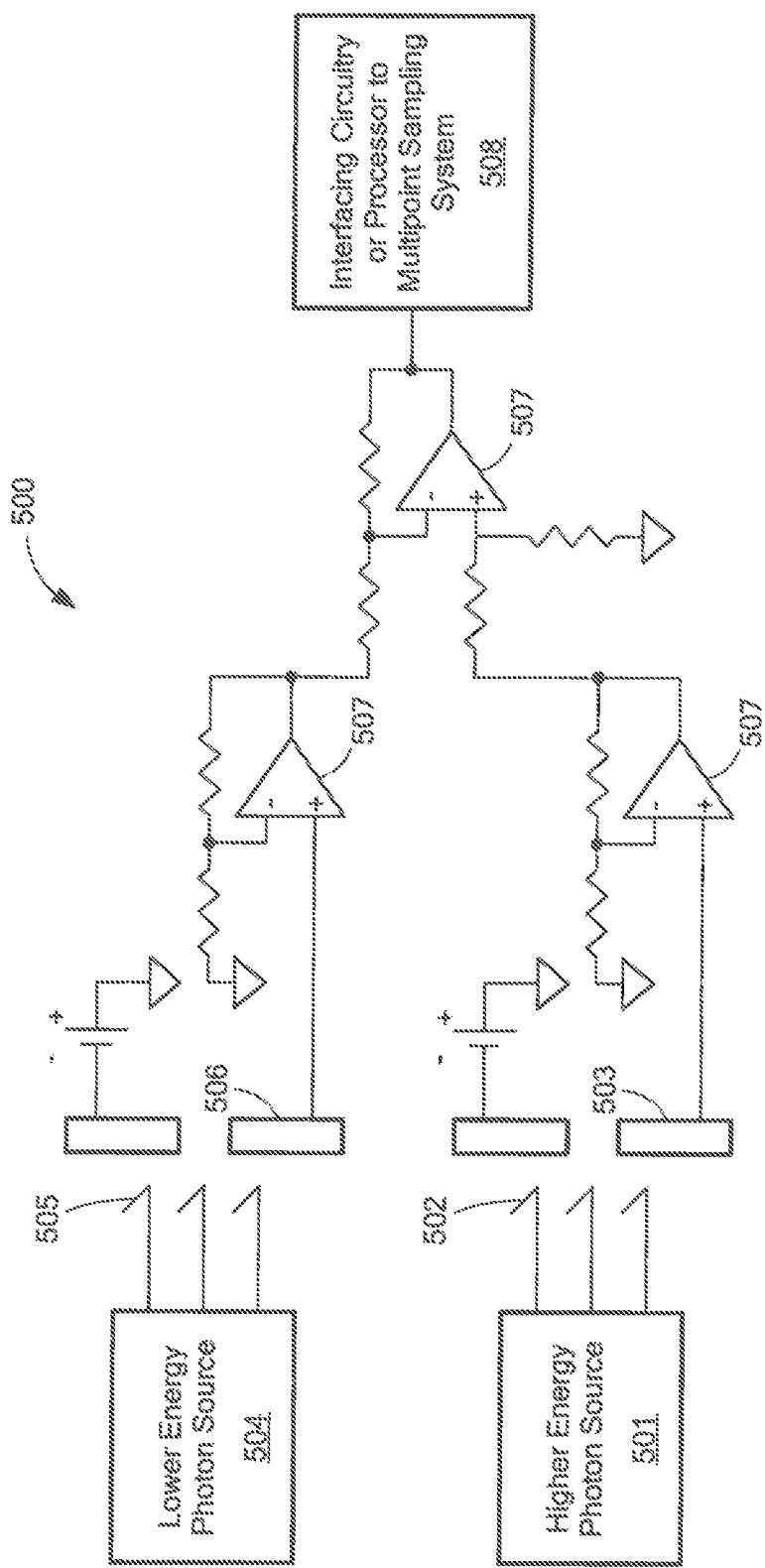
FIG. 5 is a schematic representation of an exemplary instrumentation of first and second PIDs.

FIG. 5 illustrates an example of how the electrodes of two PIDs 506 and 503 may be instrumented by a common electronic configuration 507 utilizing a differential amplifier. Those who are experienced in the art of electronics will recognize that 507 is a classic differential amplifier configuration that can be used to provide a differencing function. Note that whether the difference between the two PID measurements is made by the instrumenting electronics 507 or by the multipoint sampling system central controller 203, multipoint air sampler 301, lab ventilation controls 205, BAS 212, that these are all embodiments of the invention. In this case, even though the two electrodes share the same instrumenting electronics, the combined configuration is considered to include two PIDs.

It should be noted that PID sensors acre generally fairly expensive devices, individually costing between several hundred to several thousand dollars apiece. Therefore the application of two sensors to perform a dual PID measurement as described herein is a sensible choice for application to multipoint air sampling systems, as these multipoint architectures allow the cost of the sensors to be distributed among the plurality of locations sensed by these systems. For example, in the exemplary configuration 200, it is common for each node controller 201 to support up to 4 sensed locations and for each sensor suite 203 to support 4 to 5 node controllers 201, depending on the desired system timing. This allows the cost of a set of sensors residing in sensor suite 203 to be typically distributed across 16 to 20 locations. Thus a PID added to suite 203 which PID might cost $1000 would add only about between $50 and $60 to the cost of each sensed location.

One of the issues that can occur when applying a dual PID measurement to perform an absolute measurement of contaminants in a space such as 116 in order to provide a DCV signal is that it does not discriminate against outside contaminants that the dual PID measurement will be sensitive to. For example, the supply air provided to room 115 through duct 117 (FIG. 2) often will include contaminants which originate from outside the building that is associated with room 115 given that the air handler or fan system supplying air through plenum 101 to duct 117 supplies air that is taken from outside of the building, which may include a broad range of compounds that may be re-entrained into the associated outside air intake to the air handler that contains contaminants, such as ammonia, exhausted from other animal rooms in the facility. When there is outside influence of contaminants such as this that contributes to the contaminant levels within environment 116 a DCV signal provided to lab ventilation controls 205 in response to these outside contaminants can result in energy waste, since an increase in ventilation rates in response to these contaminants does not improve the IEQ conditions with the environment 116 of room 115.

U.S. Pat. No. 8,147,302 B2 describes how to create a DCV signal to control ventilation levels by way of making a differential measurement of air contaminants. When using a PID, it does not provide a way to distinguish against benign compounds or compounds that have less or no impact on a room's IEQ, when those compounds are generated within the environment 116. As an embodiment of this invention, further differentiation of contaminant levels is made by incorporating a dual PID measurement with differential sampling from two locations. This is accomplished by performing a dual PID measurement on contaminants within the environment 116 and subtracting that measurement from a dual PID measurement performed on the supply air provided through duct 117. This approach allows for the discrimination of compounds originating from outside the sensed environment 116 that the dual PID measurement is sensitive to, resulting in a highly specific measurement.

In one embodiment of the invention described above, the dual PID measurement is made using a first PID having a 10.6 eV lamp and a second PID having a 9.8 eV lamp. 9.8 eV lamps are common; however, the ionization signal processed by instrumentation electronics 407 will generally be much smaller for all sensed compounds than that realized when using a 10.6 eV lamp. This results in less signal resolution from the HD utilizing the 9.8 eV lamp, which affects the resolution of the dual PID measurement. Generally, higher lamp energies will also result in higher signal generated across the electrodes 405 and 404 for any PID. In one embodiment of this invention, the dual PID measurement is made using a first PID having a 10.6 eV lamp and a second PID having a 10.0 eV lamp. The use of the 10.0 eV lamp over the 9.8 eV lamp results in better sensing resolution but, it also improves the ability to provide compound discrimination of ammonia via the dual PID measurement.

To understand this further, Table 2 includes a list of the range of compounds found in chemical inventories that a dual PID measurement would be sensitive to which includes possible compounds that may either likely appear due to outside air entrainment or will likely originate within an animal room. It is further grouped by the compounds which would be detected via a dual PID measurement using PID's with 10.6 eV and 10.0 eV lamps as well as the additional compounds which would be detected via a dual PID measurement using PID's with 10.6 eV and 9.8 eV lamps. As can be seen from Table 2 there are two compounds which the dual PID will be responsive to that would naturally appear within an animal holding room, including ammonia and hydrogen sulfide. This points out another beneficial aspect to this invention, in that hydrogen sulfide is a potentially toxic compound coming from animal waste, and it is use-Rd to detect this parameter in addition to ammonia so that the ventilation rate to the animal holding room can be adjusted in response to increases in the concentration of this parameter. Along with ammonia, hydrogen sulfide is very odiferous at even low concentrations so, using the dual PID measurement, it is beneficial to not discriminate hydrogen sulfide levels from ammonia levels. This also points out another advantage in using the dual PID measurement approach over utilizing an electrochemical sensor designed for ammonia in that these electrochemical sensors often are also responsive to hydrogen sulfide but, with a negative response. That is, the presence of hydrogen sulfide, when sensed by an electrochemical sensor will often result in a reduction in the sensor's output which would cause the resulting DCV signal to lab ventilation controls 205 to erroneously be reduced rather than increased as a response to the contaminant, potentially exacerbating the IEQ conditions within the animal holding room.

Also, Table 2 helps to illustrate, the benefits of performing the dual PID measurement using a 10.6 eV PID and a 10.0 eV PID over performing the dual PID measurement using a 10.6 eV PID and a 9.8 eV PID, in that the approach using a 10.0 eV PID will be cross sensitive to fewer parameters in addition to ammonia and hydrogen sulfide. Typically, most of these parameters in Table 2 will generally exist only in small concentrations within the outside air brought into a building from the air handler. Some exceptions to this include cyclohexane and octane, which are present from combustion engine exhaust, and may at tunes be present in levels of several ppm within the outside air. Nevertheless, using either PID configuration along with the differential sampling of two dual PID measurements previously described, ensures that these outside interference compounds will be rejected from the measurement.

In some cases, due to the higher level of discrimination provided when using a 10.6 eV PID and a 10.0 eV PID to perform the dual PID measurement, the differential sampling approach may not be necessary, especially when the outside air is unlikely to contain interference compounds. This provides an added benefit of the avoidance of additional cost associated with monitoring the supply air with duct probe 208.

In addition, Table 2 shown in FIG. 7B helps to illustrate the specific utility of exemplary embodiments of the invention, it is not obvious that utilizing two PIDs in this manner would be useful, given the numerous parameters that each PID responds to including the number of parameters that the difference between their responses is responsive to. Thus, embodiments of the invention are well-suited to monitoring animal holding environments or other environments where animal waste is present.

Figure 6:
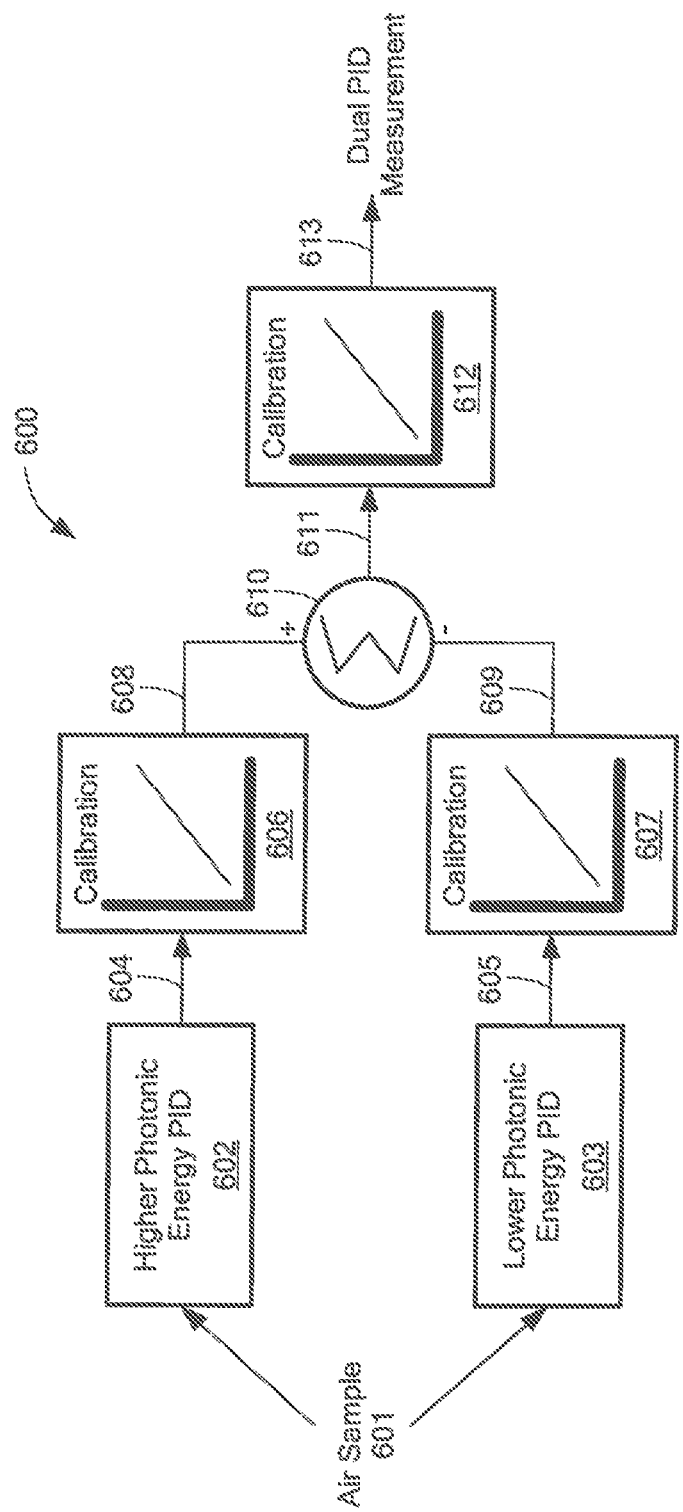
FIG. 6 is a schematic representation of an exemplary process flow to obtain a PID measurement from first and second PIDs.

FIG. 6 illustrates the signal logic involved with performing a dual PID measurement. As shown, the measurement process simultaneously exposes a higher energy PID 602 and a lower energy PID 603 to air sample 601, which is an air sample taken from a sample location (such as 210 for example) by a multipoint air sampling system. The outputs from each PID 604 and 605 are applied to their respective calibration stages 606 and 607. In one embodiment of this invention, each calibration stage 606 and 607 scale the raw PID outputs to equivalent units of isobutylene. However, the invention is not limited to providing calibrations 606 and 607 on isobutylene but it is important that the calibration parameter be a gas that the two PID's respond to in a substantially similar way and it will generally include compounds having relatively low ionization potentials compared to the ionization energy (eV) of the lower photonic energy PID 603. For example, in one embodiment, the lower energy PID's 603 lamp is a 10.0 eV lamp. Therefore, as an example, it would not be a good choice to calibrate the PID's in 600 on heptane, which ionizes at 9.92 eV. To further this explanation, there will be some margin compounds having ionization potentials close to the ionization energy of the lower photonic energy PID 603 that PID 603 will respond slightly differently to than will higher photonic energy PID 602. While these compounds, such as heptane, do not pose an issue when monitoring animal room environments 116 they simply are not good choices for calibration gases.

Referring again to FIG. 6, the dual PID measurement involves taking the calibrated output 609 of the lower photonic energy PID 603 and subtracting it from calibrated output 608 of higher photonic energy PID 602 to create a net signal 611, that is substantially a measurement of ammonia and, to a lesser extent, hydrogen sulfide as discussed, when this logic 600 and methods are applied to configuration 200 and 300. This signal 611 is then applied, to final calibration stage 612 in order to create the final dual PID measurement 613. Given that the main parameter of interest will usually be ammonia the calibration stage 612 will usually convert signal 611 to create an output signal 613 which is in units of ammonia, usually reading in ppm as ammonia or micrograms per cubic meter as ammonia, or any other system of units. This signal 613 is the signal directly used by the multipoint sampling system. In the preferred embodiment of this invention, the calibration signal logic 606, 607, and 612, and the differencing logic 610 are computations performed by central controller 203. It is understood that this logic could be performed in a wide range of ways while being considered as a part of this invention including but not limited to computing the logic 600 by the BAS 212, the lab ventilation, controls 205, within a single circuit board residing within the shared sensors 302, within control logic 303, or even remotely through internet connection 211, to name a few methods. In order to convert signal 611 into a signal 613 that is a concentration measurement of ammonia, as one embodiment of this invention, calibration stage 612 performs a conversion that is based on the higher photonic energy PID's 602 sensitivity to ammonia and, more specifically, the response factor that calibrated signal 608 has to ammonia. For example, if signal 608 is in units of ppm as isobutylene and the response factor of this output 608 to ammonia is 9.4 then, in one embodiment of this invention, calibration stage 612 converts difference signal 611 to units of ppm ammonia by multiplying signal 611 by response factor 9.4 in order to obtain dual PID measurement 613 in units of ppm as ammonia.

In one embodiment, the calibration settings in stage 612 are established by not only observing the higher photonic energy PID's 602 sensitivity to ammonia but by also observing the lower photonic energy PID's 603 finite response to ammonia. The intent of course in for PID 603 to be substantially non-responsive to ammonia; however, because of variations in hatches of lamps designed for PID 603 the actual energy output of its lamp will vary. This can be a factor for the 10.0 eV lamps given that their ideal output is close to but less than the ionization potential of ammonia which is 10.16 eV. In this embodiment the response factor of lower photonic energy PID 603 is established by way of an ammonia calibration gas. In a preferred embodiment, this response factor will be referenced to isobutylene. For example, experimental data has been established on batches of 10.0 eV PID lamps where it has been found that a PID configured with such lamps exhibited a response factor as low as 60 on ammonia as it relates to an equivalent isobutylene response. This means that the PID configured with this lamp, when exposed to 60 PPM of ammonia, would exhibit a response of 1 ppm as isobutylene. If this PID were incorporated as lower photonic energy PID 603 in logic 600 its partial response to ammonia would result in a dual PID measurement 613 that underestimates actual ammonia concentrations present. As a preferred embodiment to compensate for this, calibration stage 612 utilizes an enhanced response factor that factors the response of both sensors 602 and 603 to ammonia. This enhanced response factor is expressed as follows:

$$\text{Enhanced Response Factor} = \frac{\text{Higher Photonic Energy } PID\ RF}{1 - \frac{\text{Higher Photonic Energy } PID\ RF}{\text{Lower Photonic Energy } PID\ RF}} \quad \text{Equation 1}$$

Where:
Higher Photonic Energy PID RF is the response factor to ammonia for the higher photonic energy PID 602
Lower Photonic Energy PID RF is the response factor to ammonia for the lower photonic energy PID 603

As an example, assume a condition where air sample 601 contains 4 ppm of beta pinene and 12 ppm of ammonia. In this example assume that PID 602 operates with a 10.6 eV lamp and PID 603 operates with a 10.0 eV lamp having a RF to ammonia of 60. Assume the RF to ammonia for the 10.6 eV PID is 9.4 and that the RF's of both the 10.6 eV PID and the 10.0 eV PID's to beta pinene is 0.4. Based on this, the partial and total response of each PID to this parameters is summarized below:

|  | 10.0 eV PID | 10.6 eV PID |
|---|---|---|
| Beta Pinene Response (ppm as isobutylene) | 10 | 10 |
| Ammonia Response (ppm as isobutylene) | .2 | 1.277 |
| Combined Response (ppm as isobutylene) | 10.2 | 11.277 |

Also, the enhanced response factor in this example is calculated as:

$$\text{Enhanced Response Factor for Ammonia} = \frac{9.4}{1 - \frac{9.4}{60}} = 11.15$$

Based on this, signal 611, which is the difference between the two PID responses resolves to 1.077 ppm as isobutylene, which is multiplied by the enhanced response factor (11.15) to arrive at a value of 12 ppm as ammonia for signal 613, which is in fact the ammonia level assumed for this example.

While an exemplary embodiment of this invention involves the calculation of an enhanced response factor using Equation 1, it is understood that other mathematical approximations and numerical methods can be applied to achieve the same results and that these are therefore considered as embodiments of this invention.

In another embodiment of this invention, rather than calculating an enhanced response factor by, for example, using Equation 1, the enhanced response factor may be experimentally determined through a dual calibration procedure, whereby PIDs 602 and 603 are simultaneously exposed to the same calibration concentration of ammonia and calibration 612 is adjusted until output 613 provides an accurate reading of said calibration concentration of ammonia.

One added advantage that photoionization detector technology has over electrochemical sensor technology is that PID's can be exposed to very high levels of ammonia and other compounds, including concentration of several hundred ppm or more, without any damage incurred to the sensor. As stated previously, the useful life of electrochemical sensors generally diminishes with increases in ammonia concentrations. Further, however, electrochemical ammonia sensors have a sensing range limitation beyond which if it is exceeded the sensor will be irreversibly damaged. Here, a sensing limitation of 35 to 100 ppm ammonia is typical, beyond which, irreversible damage results. The robust capabilities of PID technology enables a dual PID measurement to be applied to more extreme environments that is not possible with conventional electrochemical sensor technology. For example, as one embodiment of this invention, a multipoint sampling system is used to provide a dual PID measurement of the exhaust air in exhaust duct 118 in order to monitor ammonia along with a limited number of other parameters, including hydrogen sulfide, associated with animal waste held within the animal cage rack 111.

Concentrations, especially of ammonia from cage racks, can be very high compared to that in the secondary environment. For example, levels of 35 ppm of ammonia or more are not uncommon and, generally, electrochemical sensors would be rapidly consumed in an environment like this, so they are not a feasible sensor choice. Providing monitoring such as this enables the collective state of the individual cages 110 to be monitored, thus ensuring better care can be provided in maintaining the cleanliness of the cages. For example, a duct probe 208 could be used by a multipoint sampling system through which air samples can be taken from the exhaust 118 of the cage rack 111 and these air samples can be conveyed through tubing 207 to node controller 201 which further conveys the air sample over tubing backbone 202 to sensor suite and central controller 203 which performs the dual PID measurement. This measurement can then be communicated through the internet 211 to a remote data center that can provide this data to a website designed to enable users to view this data by, or the information can be conveyed to the BAS 212 through which the data can be viewed, via a head-end or other remote monitoring system.

Further, as another embodiment of this invention, the dual PID measurements can be analyzed by software in order to provide notifications when ammonia levels measured from cage rack 111 through 118 exceed a predetermined value thus signifying that the bedding needs to be changed in said cages. Typically, when ammonia levels reach 25 to 40 ppm in the cage rack exhaust 118, the cages need to be changed. However, this threshold will vary depending on the types of mice being housed. This software can reside in the sensor suite and central controller 203 or remotely in a data center accessible via the internet 211, or said software may reside in lab ventilation controls 205 or BAS 212.

This provides a way to optimize the animal bedding change schedule. It turns out that bedding changes can stress animals, especially mice, and this can affect the health of the animals. Therefore bedding changes that are performed too frequently can be detrimental for this reason. Likewise, if bedding changes are not performed frequently enough, it can result in the manifestation of disease and other health effects on the animals living in the cage rack.

While exemplary embodiments of the invention are shown and described as having two PIDs, it is understood that any practical number of PIDs can be used for farther discrimination.

Figure 8:
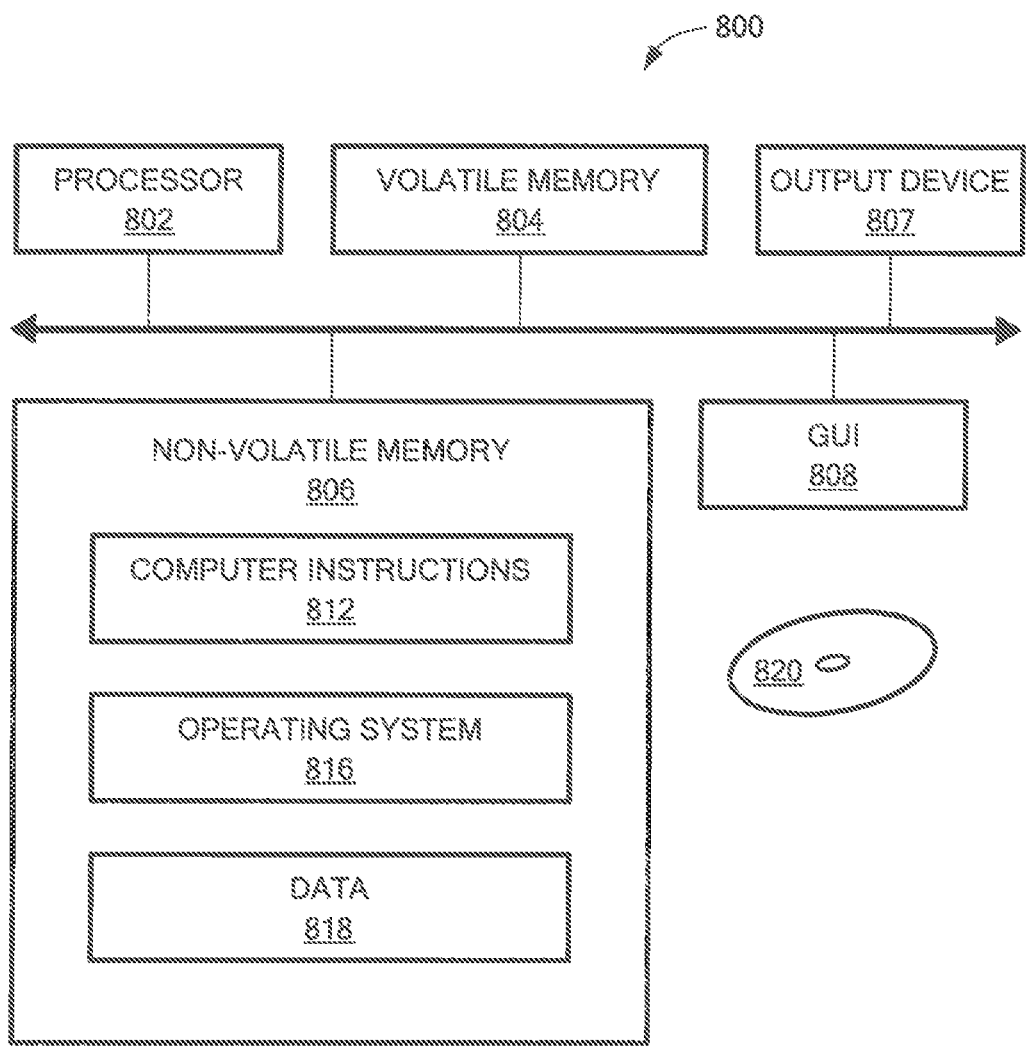
FIG. 8 is a schematic representation of an exemplary computer that can perform at least a portion of the processing described herein.

FIG. 8 shows an exemplary computer 800 that can perform at least part of the processing described herein. The computer 800 includes a processor 802, a volatile memory 804, a non-volatile memory 806 (e.g., hard disk), an output device 807 and a graphical user interface (GUI) 808 (e.g., a mouse, a keyboard, a display, for example). The non-volatile memory 806 stores computer instructions 812, an operating system 816 and data 818. In one example, the computer instructions 812 are executed by the processor 802 out of volatile memory 804. In one embodiment, an article 820 comprises non-transitory computer-readable instructions.

Processing may be implemented in hardware, software, or a combination of the two. Processing may be implemented in computer programs executed on programmable computers/machines that each includes a processor, a storage medium or other article of manufacture that is readable by the processor including volatile and non-volatile memory and/or storage elements), at least one input device, and one or more output devices. Program code may be applied to data entered using an input device to perform processing and to generate output information.

The system can perform processing, at least in part, via a computer pro am product, (e.g., in a machine-readable storage device), for execution by, or to control the operation of data processing apparatus (e.g., a programmable processor, a computer, or multiple computers). Each such program may be implemented in a hi level procedural or object-oriented programming language to communicate with a computer system. However, the programs may be implemented in assembly or machine language. The language may be a compiled or an interpreted language and it may be deployed in any form, including as a stand-alone program or as a module, component, subroutine, or other unit suitable for use in a computing environment. A computer program may be deployed to be executed on one computer or on multiple computers at one site or distributed across multiple sites and interconnected by a communication network. A computer program may be stored, on a storage medium or device (e.g., CD-ROM, hard disk, or magnetic diskette) that is readable by a general or special purpose programmable computer for configuring and operating the computer when the storage medium or device is read by the computer. Processing may also be implemented as a machine-readable storage medium, configured with a computer program, where upon execution, instructions in the computer program cause the computer to operate.

Processing may be performed by one or more programmable processors executing one or more computer programs to perform the functions of the system. All or part of the system may be implemented as, special purpose logic circuitry (e.g., an FPGA (field programmable gate array) and/or an ASIC (application-specific integrated circuit)).

Having described exemplary embodiments of the invention, it will now become apparent to one of ordinary skill in the art that other embodiments incorporating their concepts may also be used. The embodiments contained herein should not be limited to disclosed embodiments but rather should be limited only by the spirit and scope of the appended claims. All publications and references cited herein are expressly incorporated herein by reference in their entirety.

What is claimed is:

1. A method of providing a discriminating measurement of ammonia along with a limited number of secondary airborne parameters associated with animal waste from an indoor environment comprising:
    obtaining an air sample by a multipoint air sampling system which contains a representative concentration of ammonia and said other secondary airborne parameters from said environment;
    measuring said air sample by a higher photonic energy photoionization detector applied within said multipoint air sampling system to create a first photoionization detector signal;
    measuring said air sample by a lower photonic energy photoionization detector applied within said multipoint air sampling system to create a second photoionization detector signal; and
    generating a PID measurement derived from the said second photoionization detector signal and said first photoionization detector signal by subtracting the second photoionization detector signal from the first photoionization detector signal, wherein the PID measurement is proportional to the second photoionization detector signal subtracted from the first photoionization detector signal.

2. The method according to claim 1 wherein the PID measurement includes an enhanced response factor to compensate for said second photoionization detector finite response to ammonia.

3. The method of claim 1, wherein the multipoint air sampling system comprises a star configuration system.

4. The method of claim 1, wherein the multipoint air sampling system comprises a networked air sampling system.

5. The method of claim 1 wherein the higher photonic energy photoionization detector has a 10.6 eV lamp and the lower photonic energy photoionization detector has a 10.0 eV lamp.

6. The method of claim 1 wherein the indoor environment is a vivarium.

7. The method of claim 1, wherein the indoor environment comprises cage racks.

8. The method of claim 1 wherein the indoor environment is an exhaust duct connected to a cage rack which is monitored by said multipoint sampling system in order to keep track of the environmental conditions of the cages.

9. The method of claim 8, wherein the PID measurement is used to optimize the cage bedding change schedule.

10. An air sampling system, comprising:
   an air sample by a multipoint air sampling system to obtain air samples;
   a sensor suite including a higher photonic energy photoionization detector to create a first photoionization detector signal and a lower photonic energy photoionization detector to create a second photoionization detector signal; and
   a processor to generate a PID measurement from said second photoionization detector signal and said first photoionization detector signal to discriminate ammonia by subtracting the second photoionization detector signal from the first photoionization detector signal, wherein the PID measurement is proportional to the second photoionization detector signal subtracted from the first photoionization detector signal.

11. The air sampling system according to claim 10, wherein the air samples are obtained from a vivarium environment.

12. The air sampling system according to claim 11, wherein the PID measurement is used to generate an air flow signal to control air flow to the vivarium environment.

13. The air sampling system according to claim 11, wherein the PID measurement is used to derive a schedule to change animal bedding material.

14. The air sampling system according to claim 10, wherein the higher photonic energy photoionization detector has a 10.6 eV lamp and the lower photonic energy photoionization detector has a 10.0 eV lamp.

* * * * *